United States Patent
Kolomeyer et al.

(10) Patent No.: US 10,119,096 B2
(45) Date of Patent: Nov. 6, 2018

(54) SPEARMINT FLAVOR ENHANCER

(71) Applicant: Symrise Inc., Teterboro, NJ (US)

(72) Inventors: Gennadiy G. Kolomeyer, Jacksonville, FL (US); Douglas Ferone, Jacksonville, FL (US)

(73) Assignee: Symrise Inc., Teterboro, NJ (US)

( * ) Notice: Subject to any disclaimer, the term of this patent is extended or adjusted under 35 U.S.C. 154(b) by 42 days.

(21) Appl. No.: 14/821,241

(22) Filed: Aug. 7, 2015

(65) Prior Publication Data

US 2017/0035079 A1   Feb. 9, 2017

(51) Int. Cl.
| | |
|---|---|
| *A61K 8/37* | (2006.01) |
| *A61K 8/34* | (2006.01) |
| *A61K 8/35* | (2006.01) |
| *A61K 8/18* | (2006.01) |
| *A61K 47/14* | (2017.01) |
| *A61K 47/10* | (2017.01) |
| *A61K 47/08* | (2006.01) |
| *A61G 11/00* | (2006.01) |
| *C11B 9/00* | (2006.01) |
| *A61Q 11/00* | (2006.01) |
| *A23L 2/56* | (2006.01) |
| *A23L 27/00* | (2016.01) |
| *A23L 27/12* | (2016.01) |
| *A23L 27/20* | (2016.01) |

(52) U.S. Cl.
CPC .............. *C11B 9/0034* (2013.01); *A23L 2/56* (2013.01); *A23L 27/12* (2016.08); *A23L 27/203* (2016.08); *A23L 27/88* (2016.08); *A61K 8/347* (2013.01); *A61K 8/35* (2013.01); *A61K 8/37* (2013.01); *A61Q 11/00* (2013.01); *A61K 47/14* (2013.01)

(58) Field of Classification Search
None
See application file for complete search history.

(56) References Cited

U.S. PATENT DOCUMENTS

| | | | |
|---|---|---|---|
| 4,020,108 A | 4/1977 | Ehmann | |
| 4,948,595 A | 8/1990 | Patel et al. | |
| 6,835,686 B2 * | 12/2004 | Kolomeyer | ............... B01J 23/02 |
| | | | 502/102 |
| 7,355,066 B1 * | 4/2008 | Johnson | .................. C07C 67/08 |
| | | | 560/239 |
| 2005/0201953 A1 | 9/2005 | Hanada et al. | |

FOREIGN PATENT DOCUMENTS

| | | |
|---|---|---|
| EP | 0349186 A2 | 1/1990 |
| JP | 50-58031 | 2/1975 |

OTHER PUBLICATIONS

J. Wright, "Essential Oils", Chapter II of P. R. Ashurst (ed.), Food Flavorings, © Chapman & Hall 1991, p. 53.*
Jasim Uddin Chowdhury, Nemai Chandra Nandi, Minhaj Uddin and Majibur Rahman. Chemical Constituents of Essential Oils from Two Types of Spearmint (*Mentha spicata* L. and *M. cardiaca* L.) Introduced in Bangladesh. Bangladesh J. Sci. Ind. Res. 42(1), 79-82, 2007.*
Surburg H., Panten J. Common Fragrance and Flavor Materials (5th edition), 2006. pp. 217-218.
Lawrence B. New trends in essential oils. Perf. & Flav. (1980), 5 (4) pp. 6, 8, 10, 12, 14, 16.
Canova Levy, Composition of Scotch spearmint oil. Anais da Academia Brasileira de Ciencias (1972), V. 44, Issue: Suppl., pp. 273-277 (Chem. Abstracts 83:103144).
Translation of JP 50-58031.
Canova Levy, Manuscript: The Composition of Scotch spearmint oil.
PCT/US2016/045742, filing date May 8, 2016.

* cited by examiner

*Primary Examiner* — Isaac Shomer
*Assistant Examiner* — Michael P Cohen
(74) *Attorney, Agent, or Firm* — Michael P. Byrne; Timothy H. Van Dyke; Beusse Wolter Sanks & Maire

(57) ABSTRACT

Spearmint flavor enhancers and methods for the production thereof. The spearmint flavor enhancers may include l-carvone, l-carveol isomers, and d-dihydrocarveol isomers. The spearmint flavor enhancers may further include l-isocarveol isomers, l-carvyl acetate isomers, d-dihydrocarvyl acetate isomers, and l-isocarvyl acetate isomers.

15 Claims, 1 Drawing Sheet

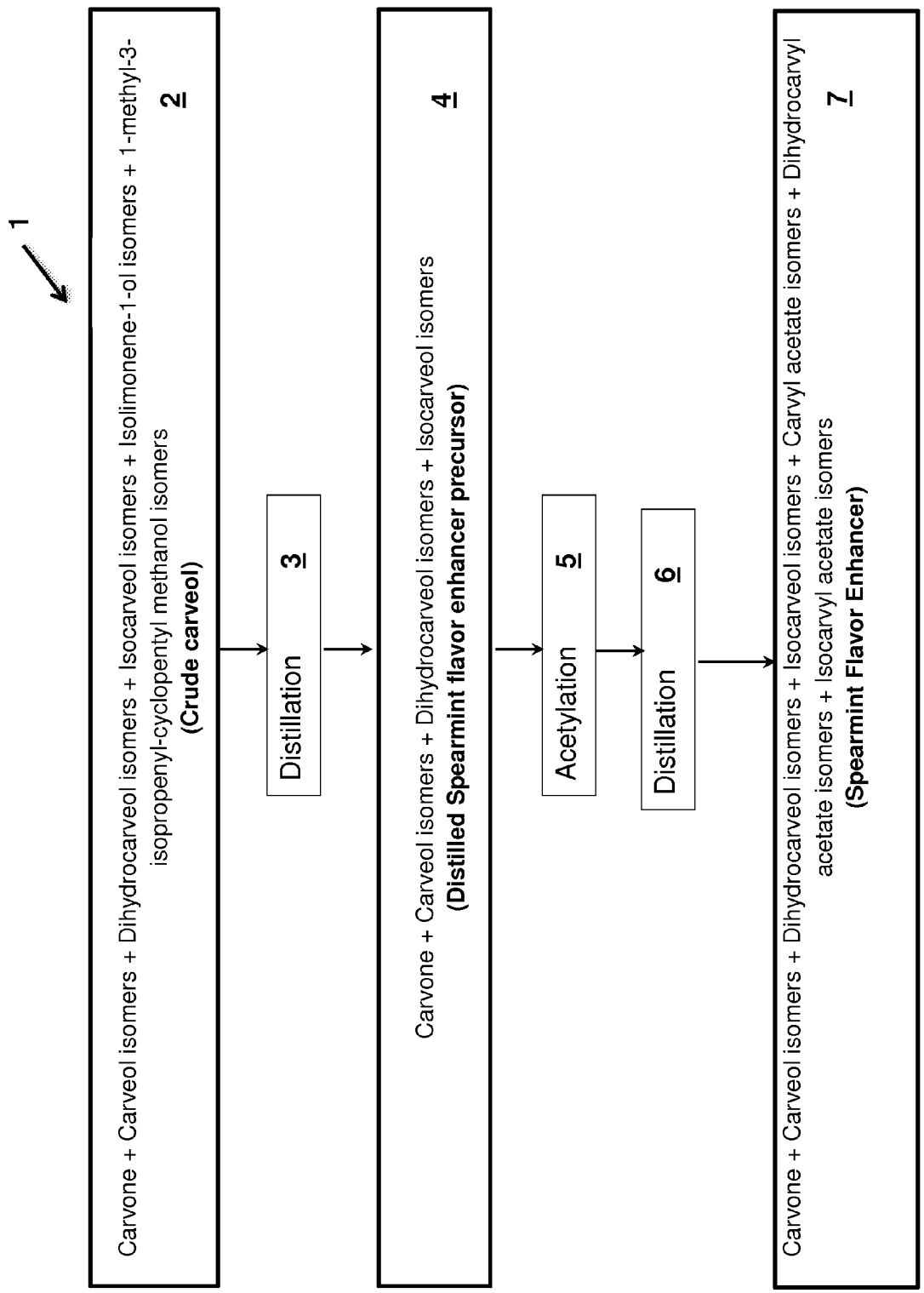

SPEARMINT FLAVOR ENHANCER

FIELD

The disclosure relates generally to flavor ingredients suitable for food, confectionery, oral care, cosmetics, and pharmaceutical products such as candy, alcoholic and non-alcoholic beverages, chewing gum, toothpaste or gel, mouthwash, confectionaries, creams, lotions, and pharmaceutical preparations; and more specifically to flavor ingredients with spearmint taste and odor.

BACKGROUND

Spearmint flavors are widely used in food, confectionary, oral care, cosmetics, and pharmaceutical products. Commonly, natural spearmint oils are used to achieve the desirable rich and natural spearmint flavor. Alternatively, complex mixtures of natural and synthetic ingredients or only synthetic ingredients can be used to create the spearmint flavor.

Natural spearmint oils are available in the marketplace. However, their production volume, composition, and price significantly vary depending on area planted, weather conditions, oil yield, and other factors. Natural oils cannot satisfy the demand for spearmint flavors and are relatively expensive. The only readily available synthetic ingredient with spearmint flavor is l-carvone. While l-carvone represents about 60-75% of spearmint oil, it doesn't provide the distinct odor and flavor of the natural spearmint oil, which in addition to l-carvone contains carveol (0.4-0.7%), carvyl acetate (1-2%), dihydrocarveol (0.1-0.2%), and dihydrocarvyl acetate (0.3-0.4%) among many other components. The synthetic versions of these compounds are offered commercially. However, their use is limited due to high prices reaching a few hundred dollars per kilogram.

Preparation of synthetic spearmint ingredient such and carveol, carvyl acetate, dihydrocarveol, and dihydrocarvyl acetate involves a few chemical steps and special catalysts and reagents. Some commonly used synthetic approaches are shown on Scheme 1.

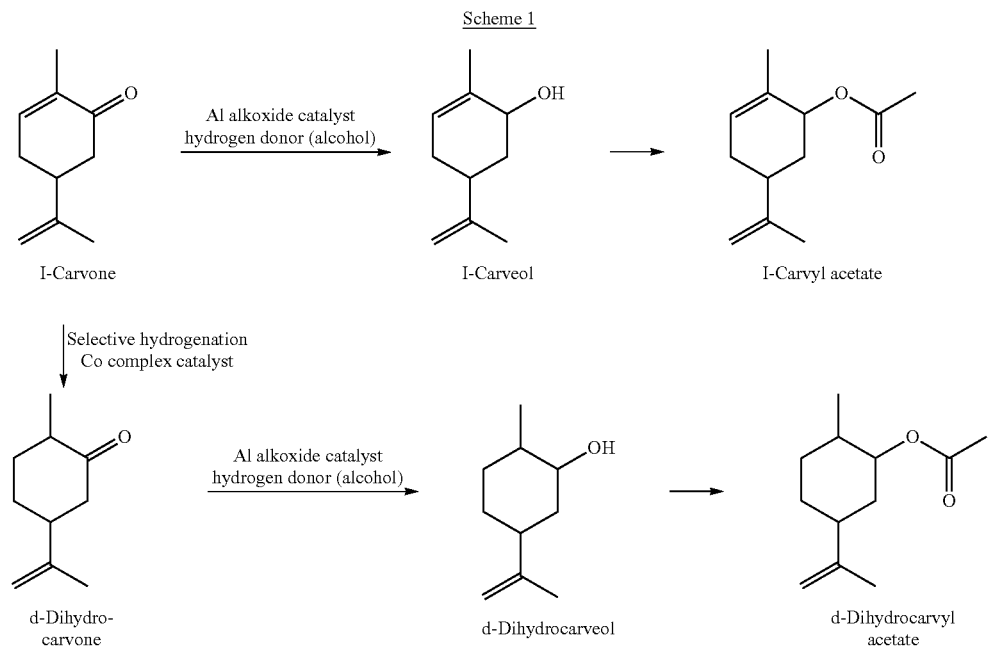

Thus, preparation of carvyl acetate involves two chemical steps, one of which requires a large amount of the aluminum alkoxide catalyst and an excess of an auxiliary alcohol. This process generates a large amount of organic waste and highly contaminated wastewater. Furthermore, the preparation of d-dihydrocarvyl acetate is a three step chemical process. It starts with a selective hydrogenation of l-carvone to d-dihydrocarvone, which requires a specially prepared cobalt complex catalyst. The rest of the process possesses the same disadvantages as the l-carvyl acetate process.

These two components, l-carvyl acetate and d-dihydrocarvyl acetate, are essential for creating the distinct spearmint flavor. However, due to the complex technology and high prices they can't be extensively used in flavor applications. Therefore, development of a commercially viable, economical, and green process for the preparation of these compounds or their mixtures is essential for satisfying the needs of flavor industry.

BRIEF DESCRIPTION OF THE DRAWINGS

These and other features, aspects, and advantages of the present disclosure will become better understood with reference to the following description and appended claims, and accompanying drawings where:

FIG. 1: shows a schematic process flow diagram for preparing a spearmint flavor enhancer according to certain embodiments.

It should be understood that the various embodiments are not limited to the arrangements and instrumentality shown in the drawings.

DETAILED DESCRIPTION

The present disclosure may be understood more readily by reference to the following detailed description of preferred embodiments of the disclosure as well as to the examples included therein. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant FIGURE.

Various embodiments relate to a spearmint flavor enhancer that may include l-carvone, l-carveol isomers, and d-dihydrocarveol isomers. The spearmint flavor enhancer may further include l-isocarveol isomers, l-carvyl acetate isomers, d-dihydrocarvyl acetate isomers, and l-isocarvyl acetate isomers.

The l-carvone may be present in an amount within a range having a lower limit and/or an upper limit. The range can include or exclude the lower limit and/or the upper limit. The lower limit and/or upper limit can be selected from about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, and 98 percent by weight based on the total weight of the spearmint flavor enhancer. For example, according to certain preferred embodiments, the l-carvone may be present in an amount of from 0-95 percent by weight based on the total weight of the spearmint flavor enhancer. As another non-limiting example, the spearmint flavor enhancer may include from 20-50 percent by weight of l-carvone.

The l-carveol isomers may be present in an amount within a range having a lower limit and/or an upper limit. The range can include or exclude the lower limit and/or the upper limit. The lower limit and/or upper limit can be selected from about 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, and 10 percent by weight based on the total weight of the spearmint flavor enhancer. For example, according to certain preferred embodiments, the l-carveol isomers may be present in an amount of from 0-5 percent by weight based on the total weight of the spearmint flavor enhancer. As another non-limiting example, the spearmint flavor enhancer may include from 0.01-2 percent by weight of l-carveol isomers.

The d-dihydrocarveol isomers may be present in an amount within a range having a lower limit and/or an upper limit. The range can include or exclude the lower limit and/or the upper limit. The lower limit and/or upper limit can be selected from about 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 percent by weight based on the total weight of the spearmint flavor enhancer. For example, according to certain preferred embodiments, the d-dihydrocarveol isomers may be present in an amount of from 0-2 percent by weight based on the total weight of the spearmint flavor enhancer. As another non-limiting example, the spearmint flavor enhancer may include from 0-2 percent by weight of d-dihydrocarveol isomers.

The l-isocarveol isomers may be present in an amount within a range having a lower limit and/or an upper limit. The range can include or exclude the lower limit and/or the upper limit. The lower limit and/or upper limit can be selected from about 0, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, and 3 percent by weight based on the total weight of the spearmint flavor enhancer. For example, according to certain preferred embodiments, the l-isocarveol isomers may be present in an amount of from 0-1 percent by weight based on the total weight of the spearmint flavor enhancer. As another non-limiting example, the spearmint flavor enhancer may include from 0-0.1 percent by weight of l-isocarveol isomers.

The l-carvyl acetate isomers may be present in an amount within a range having a lower limit and/or an upper limit. The range can include or exclude the lower limit and/or the upper limit. The lower limit and/or upper limit can be selected from about 0, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, and 98 percent by weight based on the total weight of the spearmint flavor enhancer. For example, according to certain preferred embodiments, the l-carvyl acetate isomers may be present in an amount of from 0.1-95 percent by weight based on the total weight of the spearmint flavor enhancer. As another non-limiting example, the spearmint flavor enhancer may include from 30-75 percent by weight of l-carvyl acetate isomers.

The d-dihydrocarvyl acetate isomers may be present in an amount within a range having a lower limit and/or an upper limit. The range can include or exclude the lower limit and/or the upper limit. The lower limit and/or upper limit can be selected from about 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 percent by weight based on the total weight of the spearmint flavor enhancer. For example, according to certain preferred embodiments, the d-dihydrocarvyl acetate isomers may be present in an amount of from 0.1-2 percent by weight based on the total weight of the spearmint flavor enhancer. As another non-limiting example, the spearmint flavor enhancer may include from 0.01-4 percent by weight of d-dihydrocarvyl acetate isomers.

The l-isocarvyl acetate isomers may be present in an amount within a range having a lower limit and/or an upper limit. The range can include or exclude the lower limit and/or the upper limit. The lower limit and/or upper limit can be selected from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, and 15 percent by weight based on the total weight of the spearmint flavor enhancer. For example, according to certain preferred embodiments, the l-isocarvyl acetate isomers may be present in an amount of from 0.1-10 percent by weight based on the total weight of the spearmint flavor enhancer. As another non-limiting example, the spearmint flavor enhancer may include from 0.1-5 percent by weight of l-isocarvyl acetate isomers.

The spearmint flavor enhancer may be "substantially free" of iso-Limonen-1-ol isomers. The spearmint flavor enhance may be "substantially free" of 1-methyl-3-isopropenyl-cyclopentyl methanol isomers. As used herein, the term "substantially free" refers to a component that is completely absent from the spearmint flavor enhancer or that is present in a limited amount. The limited amount can be less than 0.1 percent by weight based on the total weight of the spearmint flavor enhancer. As another non-limiting example, the limited amount may be less than 0.05% by weight.

The spearmint flavor enhancer may be incorporated into any product. The spearmint flavor enhance may be incorporated into a flavor composition. Similarly, the flavor composition may be incorporated into any product. The product may include, but is not limited to an oral care product, a mouthwash, a toothpaste, a confectionery, a dental floss, chewing gum, a beverage, a cosmetic, a cream, a lotion, a gel, a pharmaceutical, and combinations thereof.

The spearmint flavor enhancer may be present in the flavor composition in an amount within a range having a lower limit and/or an upper limit. The range can include or exclude the lower limit and/or the upper limit. The lower limit and/or upper limit can be selected from about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75 percent by weight based on the total weight of the flavor composition. For example, according to certain preferred embodiments, the spearmint flavor enhancer may be present in the flavor composition in an amount of from 0.01 to 50 percent by weight based on the total weight of the flavor composition.

The spearmint flavor enhancer may be present in the product in an amount within a range having a lower limit and/or an upper limit. The range can include or exclude the lower limit and/or the upper limit. The lower limit and/or upper limit can be selected from about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75 percent by weight based on the total weight of the product. For example, according to certain preferred embodiments, the spearmint flavor enhancer may be present in the product in an amount of from 0.01 to 50 percent by weight based on the total weight of the product.

Various embodiments relate to methods that can include: fractionating crude carveol to produce a plurality of distillation fractions; combining a selected group of one or more of the plurality of distillation fractions to produce a mixture; acetylating the mixture to produce an acetylation product; and fractionating the acetylation product to obtain a spearmint flavor enhancer. The crude carveol may be obtained from any source, but according to some embodiments, the crude carveol may be obtained by a d-limonene oxide rearrangement reaction. The crude carveol may include l-carvone, l-carveol isomers, and d-dihydrocarveol isomers. The crude carveol may further include one or more cyclic alcohols. The one or more cyclic alcohols may include isolimonene-1-ol isomers, 1-methyl-3-isopropenyl-cyclopentyl methanol isomers, isocarveol isomers, and combinations thereof. According to some embodiments, the selected group of one or more of the plurality of distillation fractions may include l-isocarveol isomers. According to various embodiments, fractionating the acetylation product comprises removing acetic acid formed in the acetylating step.

The spearmint flavor enhancer produced by the methods described herein may have the same composition as the spearmint flavor enhancers disclosed in any of the various embodiments disclosed herein. The spearmint flavor enhancer may include, for example, l-carvone, l-carveol isomers, l-carvyl acetate isomers, d-dihydrocarveol isomers, d-dihydrocarvyl acetate isomers, and l-isocarvyl acetate isomers. As a more specific, but non-limiting example, the spearmint flavor enhancer can include 0-95 percent by weight of l-carvone, 0-5 percent by weight of l-carveol isomers, and 0-2 percent by weight of d-dihydrocarveol isomers. As in other embodiments, the spearmint flavor enhancer may further include 0-1 percent by weight of l-isocarveol isomers, 0.1-95 percent by weight of l-carvyl acetate isomers, 0.1-2 percent by weight of d-dihydrocarvyl acetate isomers, and 0.1-10 percent by weight of l-isocarvyl acetate isomers.

A spearmint flavor enhancer produced by a process including fractionating crude carveol to produce a plurality of distillation fractions; combining a selected group of one or more of the plurality of distillation fractions to produce a mixture; acetylating the mixture to produce an acetylation product; and fractionating the acetylation product to obtain the spearmint flavor enhancer, wherein the spearmint flavor enhancer is as identified in any other embodiment disclosed herein.

Various embodiments relate to a mixture of l-carvone, l-carveol isomers, l-carvyl acetate isomers, d-dihydrocarveol isomers, d-dihydrocarvyl acetate isomers, and l-isocarvyl acetate isomers. The mixture may be partially or completely obtained through a single, simple chemical reaction from crude l-carveol formed in the d-limonene oxide rearrangement. In addition to a few typical spearmint oil components this mixture also contains l-isocarvyl acetate isomers, which are only occasionally found in the natural spearmint oils in very low concentrations. Unexpectedly, this unique mixture possesses a very strong characteristic flavor and odor characteristic for natural spearmint oil although it doesn't contain all the components of natural spearmint oil. This mixture can be used to enrich natural spearmint oil or bring about or enhance the natural sweet herbaceous spearmint note in the synthetic flavor compositions.

The d-limonene oxide rearrangement leads to a formation of a complex mixture of products designated here as crude carveol that contains l-carvone, l-carveol isomers, and d-dihydrocarveol isomers, which are components of the spearmint oil and can be used as precursors for l-carvyl acetate and d-dihydrocarvyl acetate. However, crude carveol also contains a number of other cyclic alcohols such as isolimonene-1-ol isomers, 1-methyl-3-isopropenyl-cyclopentyl methanol isomers, and isocarveol isomers. Heretofore, these alcohols and their esters have not been found in the natural spearmint oils. Therefore, it was unexpected that crude carveol could be converted into a product that would be a valuable spearmint flavor ingredient and enhancer.

Various embodiments relate to fractionating crude carveol in such a way that the components unrelated to spearmint oil can be removed, while the distillation fractions containing spearmint related compounds can be combined and further processed to obtain the spearmint flavor enhancer. Surprisingly, fractions containing l-isocarveol isomers—not a typical component of spearmint oil—can also be included to give rise to l-isocarvyl acetate, which provides a valuable fresh spearmint odor and flavor in the final product.

The combined fractions from crude carveol distillation (a mixture of l-carvone, l-carveol, d-dihydrocarveol, and l-isocarveol) were acetylated with acetic anhydride. In this reaction l-carvone remains unchanged, while l-carveol isomers, d-dihydrocarveol isomers, and l-isocarveol isomers can be converted to the corresponding acetates partially or completely depending on the amount of acetic anhydride used. The acetylation product, designated here as crude spearmint flavor enhancer, was fractionated to remove the acetic acid formed in the acetylation process and the excess of acetic anhydride and obtain the final product, i.e. distilled spearmint flavor enhancer. The structures of compounds mentioned in this disclosure are presented in Table 1.

Acetylation refers to the process of introducing an acetyl group (resulting in an acetoxy group) into a compound, namely the substitution of an acetyl group for an active hydrogen atom. For example, a reaction involving the replacement of the hydrogen atom of a hydroxyl group with an acetyl group ($CH_3 CO$) yields a specific ester, the acetate. Acetic anhydride may be used as an acetylating agent reacting with free hydroxyl groups. Any acetylation agent such as acetic acid, acetic anhydride, acetyl chloride and others can be employed. The acetylation can be achieved by trans-esterification. The process can use a catalyst such as an acid, a base, an amine, or an imidazole derivatives. The temperature range of the acetylation may be from 20-180 degrees Celsius.

TABLE 1

| Name | Structure | Collective name |
| --- | --- | --- |
| l-Carvone | | Carvone |
| trans-l-Carveol (R = H) trans-l-Carvyl acetate (R = Ac) | 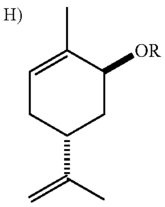 | Carveol isomers (R = H) and Carvyl acetate isomers (R = Ac) |
| cis-l-Carveol (R = H) cis-l-Carvyl acetate (R = Ac) | 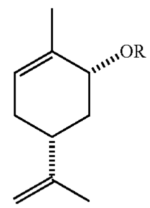 | |
| trans-l-Isocarveol (R = H) trans-l-Isocarvyl acetate (R = Ac) | 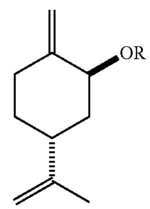 | Isocarveol isomers (R = H) and Isocarvyl acetate isomers (R = Ac) |
| cis-l-Isocarveol (R = H) cis-l-Isocarvyl acetate (R = Ac) | 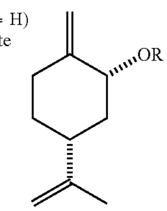 | |
| d-Dihydrocarveol (R = H) d-Dihydrocarvyl acetate (R = Ac) | 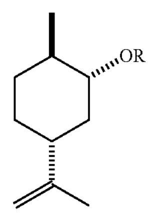 | Dihydrocarveol isomers (R = H) and Dihydrocarvyl acetate isomers (R = Ac) |
| neo-d-Dihydrocarveol (R = H) neo-d-Dihydrocarvyl acetate (R = Ac) | 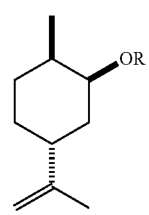 | |
| iso-d-Dihydrocarveol (R = H) iso-d-Dihydrocarvyl acetate (R = Ac) | 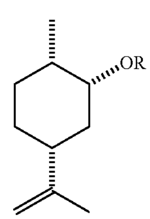 | |

TABLE 1-continued

| Name | Structure | Collective name |
|---|---|---|
| neo,iso-d-Dihydrocarveol (R = H) neo,iso-d-Dihydrocarvyl acetate (R = Ac) | 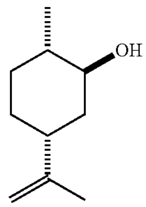 | |
| cis-and trans-iso-Limonene-1-ol | 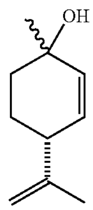 | iso-Limonen-1-ol isomers |
| cis- and trans-1-methyl-3-isopropenyl-cyclopentyl methanol | 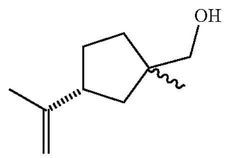 | 1-methyl-3-isopropenyl-cyclopentyl methanol isomers |

As illustrated in the flow diagram of FIG. 1, the process 1 for the spearmint flavor enhancer preparation includes providing crude carveol 2. The crude carveol 2 may be obtained by d-limonene oxide rearrangement. The process further includes distillation or fractionation 3 of the crude carveol and combining the select distillation fractions suitable for further processing to spearmint flavor enhancer. Distillation/fractionation and re-blending the fractions may serve two purposes. First, all components unrelated to spearmint oil and having undesirable flavor can be removed. For example, cis- and trans-iso-Limonene-1-ol and cis- and trans-1-methyl-3-isopropenyl-cyclopentyl methanol (see page 4 lines 5-7). Secondly, distillation/fractionation and re-blending can create a desirable ratio between the l-carveol and d-dihydrocarveol. Blending only the certain cuts allows for varying the odor and flavor to achieve the desirable organoleptic effect. Next, the combined fractions may be subjected to acetylation 5 and a subsequent distillation or fractionation 6. The result may be the finished distilled spearmint flavor enhancer 7.

According to various embodiments, the process of present invention involves only one very simple chemical step starting from the commercially available crude carveol intermediate. The process generates a very small amount of by-products and is green and environmentally friendly. In one chemical step, the process can yield a complex mixture of compounds with strong, fresh, rich, and valuable spearmint flavor as opposed to other known processes that involve multiple chemical steps and lead to only individual components that do not possess the same complex flavor characteristics as the spearmint flavor enhancer according to various embodiments.

The spearmint flavor enhancer obtained by the above described process contains a unique combination of l-carvone, l-carveol isomers, l-carvyl acetate isomers, d-dihydrocarveol, d-dihydrocarvyl acetate isomers, and l-isocarvyl acetate isomers. The process is flexible and allows to modify the composition on every step. Depending on the distillation conditions, selection of cuts for blending, and the degree of acetylation, a wide range of combinations of the components in the finished spearmint flavor enhancer is attainable.

The spearmint flavor enhancer of this invention contains 0-95% l-carvone, 0-5% l-carveol isomers, 0-2% d-dihydrocarveol isomers, 0-1% l-isocarveol isomers, 0.1-95% l-carvyl acetate isomers, 0.1-2% d-dihydrocarvyl acetate isomers, and 0.1-10% l-isocarvyl acetate isomers. The preferred composition of the spearmint flavor enhancer is 20-50% l-carvone, 0.01-2% l-carveol isomers, 0-2% d-dihydrocarveol isomers, 0-0.1% l-isocarveol isomers, 30-75% l-carvyl acetate isomers, 0.01-4% d-dihydrocarvyl acetate isomers, and 0.1-5% l-isocarvyl acetate isomers.

Flavor compositions, which contain Spearmint flavor enhancer of present invention, can be used in varieties of applications where a fresh, herbaceous, spearmint notes are desirable. Such flavors include but not limited to spearmint, peppermint, and other mint as well as floral flavors. Such applications include but not limited to oral care products, mouthwashes, toothpastes, flosses, chewing gums, beverages, cosmetics, creams, lotions, gels, pharmaceuticals, etc.

EXAMPLES

The following examples demonstrate that the spearmint flavor enhancers according to various embodiments can be valuable ingredients for creating spearmint flavors. The spearmint flavor enhances may be used to impart the natural spearmint oil notes in composition that don't contain any natural oils or to enhance these notes when the natural oil is present. The spearmint flavor enhancers may be more cost efficient and, in contrast with the natural spearmint oil, is independent from whether condition, crop yield, and more consistent in composition.

Example 1

This example demonstrates the preparation of a spearmint flavor enhancer. The particular spearmint flavor enhancer contained 36.83% l-carvone, 0.44% l-carveol isomers, 0.06% d-dihydrocarveol isomers, 0.09% l-isocarveol isomers, 57.68% l-carvyl acetate isomers, 1.29% d-dihydrocarvyl acetate isomers, and 3.08% l-isocarvyl acetate isomers. This product is referred to as Spearmint flavor enhancer A.

The following steps A)-C) were employed:
A) Crude carveol was prepared by d-limonene oxide rearrangement according to example 38 of U.S. Pat. No. 6,835,686.
B) Crude carveol obtained in step A was fractionated of a packed distillation column with efficiency 25 theoretical plates at a residual pressure of 1 mm Hg. The distillation fractions were combined in such a way that the resulting mixture contained 1.5% l-carvone, 91.2% l-carveol isomers, 2.4% d-dihydrocarveol isomers, and 4.6% l-isocarveol isomers.
C) The mixture obtained in step B (3000 g) was combined with 3000 g of l-carvone and heated up to 120° C. with agitation. To this mixture 2500 g of acetic anhydride was added over 2 hours while the reaction temperature was maintained at 120° C. The reaction mixture was agitated at 120° C. for 2 more hours and cooled to ambient temperature. The acetylation product was fractionated using a packed distillation column with efficiency 12 theoretical plates. The acetic acid was removed at a residual pressure of about 100 mm Hg, while the remaining components were fractionated at 1 mm Hg. The collected fractions were combined in such a way that the resulting spearmint flavor enhancer (3570 g) contained 36.83% l-carvone, 0.44% l-carveol isomers, 0.06% d-dihydrocarveol isomers, 0.09% l-isocarveol isomers, 57.68% l-carvyl acetate isomers, 1.29% d-dihydrocarvyl acetate isomers, and 3.08% l-isocarvyl acetate isomers. This product is referred to as Spearmint flavor enhancer A in the examples below.

Example 2

This example evaluates a model spearmint flavor for oral care products without natural spearmint oil. More specifically, the impact of the Spearmint flavor enhancer A on flavor composition was evaluated. Example 2 demonstrates benefits of the addition of Spearmint flavor enhancer A to a model flavor composition for toothpaste. The original composition 2-1 that didn't contain any natural spearmint oil had flat flavor characteristic and was lacking the natural spearmint note. The composition 2-2, which was based on 2-1 but in addition contained Spearmint flavor enhancer, had a fresh, bright character with natural notes reminiscent of the natural spearmint oil.

A model flavor composition 2-1, which contains Spearmint flavor enhancer A, was prepared and compared with a control composition 2-2 in which Spearmint flavor enhancer was replaced with an odorless and flavorless compound propylene glycol. The results are summarized in Table 2:

TABLE 2

|  | Composition 2-1 % | Control composition 2-2 % |
| --- | --- | --- |
| l-Menthol | 25 | 25 |
| l-Carvone | 57 | 57 |
| Spearmint flavor enhancer A | 8 | 0 |
| Propylene glycol | 0 | 8 |
| Anethole | 10 | 10 |
| Total | 100 | 100 |
| Flavor characteristics | Strong spearmint with fresh, herbaceous, and natural spearmint notes | Spearmint, flat |

Example 3

This example evaluates a model spearmint flavor for confectionary products. More specifically, Example 3 demonstrates that addition of a small amount of Spearmint flavor enhancer A allows to reduce the use of the natural spearmint oil in a composition without sacrificing the flavor quality, which still possesses a very distinct natural spearmint oil notes. The results are summarized in Table 3:

TABLE 3

|  | Composition 3-1 % | Control composition 3-2 % |
| --- | --- | --- |
| l-Menthol | 25 | 25 |
| l-Carvone | 49 | 49 |
| Spearmint oil natural, Native type | 1.5 | 16 |
| Spearmint flavor enhancer A | 6.5 | 0 |
| Propylene glycol | 8 | 0 |
| Anethole | 10 | 10 |
| Total | 100 | 100 |

TABLE 3-continued

|  | Composition 3-1 % | Control composition 3-2 % |
| --- | --- | --- |
| Flavor characteristics | Strong spearmint with fresh, herbaceous, and natural spearmint notes | Strong spearmint with fresh, herbaceous, and natural spearmint notes |

Example 4

This example evaluates a model spearmint/peppermint flavor for chewing gum. More specifically, Example 4 demonstrates the impact of Spearmint flavor enhancer on a more complex Spearmint/Peppermint (double mint) flavor. Results confirm that natural spearmint oil can be completely or partially eliminated and replaced with Spearmint flavor enhancer A without losing the fresh, herbaceous, and natural notes of the natural spearmint oil. The results are summarized in Table 4:

TABLE 4

|  | Composition 4-1 % | Composition 4-2 % | Control composition 4-3 % |
| --- | --- | --- | --- |
| l-Menthol | 30 | 30 | 30 |
| Peppermint oil, natural | 10 | 10 | 10 |
| l-Carvone | 30 | 30 | 30 |
| Spearmint flavor enhancer A | 10 | 8 | 0 |
| Anethole | 10 | 10 | 10 |
| Spearmint oil natural, Native type | 0 | 2 | 20 |
| Propylene glycol | 10 | 10 | 0 |
| Total | 100 | 100 | 100 |
| Flavor characteristics | Strong mint and spearmint with fresh, herbaceous, and natural spearmint notes | Strong mint and spearmint with fresh, herbaceous, and natural spearmint notes | Strong mint and spearmint with fresh, herbaceous, and natural spearmint notes |

Although the present invention has been described in considerable detail with reference to certain preferred versions thereof, other versions are possible. Therefore, the spirit and scope of the appended claims should not be limited to the description of the preferred versions contained herein. All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A method for obtaining a spearmint flavor enhancer comprising the following steps:
   (i) fractionating crude carveol to produce a first plurality of distillation fractions;
   (ii) combining a selected group of one or more of the first plurality of distillation fractions rich in l-carvone, l-carveol, d-dihydrocarveol, and l-isocarveol to produce a mixture;

(iii) acetylating the mixture to produce an acetylation product;
(iv) fractionating the acetylation product to produce a second plurality of distillation fractions, and
(v) combining a selected group of one or more of the second plurality of distillation fractions to obtain said spearmint flavor enhancer,
wherein said spearmint flavor enhancer shows the following composition:
(a) about 30 to about 50 percent by weight of l-carvone, and
(b) about 50 to about 70 percent by weight of l-carvyl acetate isomers,
on condition that the amounts add, optionally with further constituents, to 100 percent by weight.

2. The method according to claim 1, wherein the crude carveol is obtained by a d-limonene oxide rearrangement reaction.

3. The method according of claim 1, wherein the crude carveol comprises l-carvone, l-carveol isomers, and d-dihydrocarveol isomers.

4. The method according to claim 3, wherein the crude carveol further comprises one or more cyclic alcohols.

5. The method according to claim 4, wherein the one or more cyclic alcohols are selected from the group consisting of isolimonene-l-ol isomers, 1-methyl-3-isopropenyl-cyclopentyl methanol isomers, and isocarveol isomers.

6. The method according to claim 1, wherein the selected group of one or more of the plurality of distillation fractions comprise l-isocarveol isomers.

7. The method according to claim 1, wherein the spearmint flavor enhancer comprises less than 0.1% by weight of iso-Limonen-l-ol isomers.

8. The method according to claim 1, wherein the spearmint flavor enhance comprises less than 0.1% by weight of 1-methyl-3-isopropenyl-cyclopentyl methanol isomers.

9. The method according to claim 8, wherein fractionating the acetylation product comprises removing acetic acid formed in the acetylating step.

10. The method of claim 1, wherein said spearmint flavor enhancer further comprises 0.1 to about 5 percent by weight of l-carveol isomers.

11. The method of claim 1, wherein said spearmint flavor enhancer further comprises 0.1 to about 2 percent by weight of d-dihydrocarveol isomers.

12. The method of claim 1, wherein said spearmint flavor enhancer further comprises 0.1 to about 1 percent by weight of l-isocarveol isomers.

13. The method of claim 1, wherein said spearmint flavor enhancer further comprises 0.1 to about 2 percent by weight of d-dihydrocarvyl acetate isomers.

14. The method of claim 1, wherein said spearmint flavor enhancer further comprises 0.1 to about 10 percent by weight of l-isocarvyl acetate isomers.

15. The method of claim 1, wherein the l-carveol isomers, dihydrocarveol isomers and l-isocarveol isomers are converted to the corresponding acetates partially or completely.

* * * * *